(12) United States Patent
Casscells, III et al.

(10) Patent No.: US 6,454,707 B1
(45) Date of Patent: Sep. 24, 2002

(54) METHOD AND APPARATUS FOR PREDICTING MORTALITY IN CONGESTIVE HEART FAILURE PATIENTS

(75) Inventors: Samuel W. Casscells, III, 3656 Wickersham La., Houston, TX (US) 77027; Monteza Naghavi; M. Said Siadaty, both of Houston, TX (US)

(73) Assignee: Samuel W. Casscells, III, Houston, TX (US)

( * ) Notice: Subject to any disclaimer, the term of this patent is extended or adjusted under 35 U.S.C. 154(b) by 0 days.

(21) Appl. No.: 09/519,122

(22) Filed: Mar. 6, 2000

Related U.S. Application Data

(60) Provisional application No. 60/123,342, filed on Mar. 8, 1999.

(51) Int. Cl.[7] .................................................. A61B 5/00
(52) U.S. Cl. ...................................................... 600/300
(58) Field of Search ................................. 600/549, 587, 600/300

(56) References Cited

U.S. PATENT DOCUMENTS

| | | | |
|---|---|---|---|
| 4,216,462 A | 8/1980 | McGrath et al. |
| 4,508,103 A | 4/1985 | Calisi |
| 4,763,112 A | 8/1988 | Hsieh |
| 4,981,139 A | 1/1991 | Pfohl |
| 5,108,423 A | 4/1992 | Lu |
| 5,241,965 A | 9/1993 | Mick |
| 5,464,012 A | 11/1995 | Falcone |

OTHER PUBLICATIONS

Pierpont GL, Parenti CM. Physician risk assessment and APACHE scores in cardiac care units. Clin Cardiol 1999; 22:366–8.

Robbins M, Francis G, Pashkow FJ, et al. Ventilatory and heart rate responses to exercise: better predictors of heart filure mortality than peak oxygen consumption. Circulation 1999; 100:2411–7.

Senni M, Tribouilloy CM, Rodeheffer RJ, et al. Congestive heart failure in the community: a study of all incident cases in Olmstead Country, Minnesota, in 1991. Circulation 1998; 98:2282–9.

Shellock FG, Rubin SA, Ellrodt AG, Muchlinski A, Brown H, Swan HJ. Unusual core temperature decreasein exercising heart–failure patients. J Appl Physiol 1983; 54:544–50.

Shellock FG, Rubin SA. Mixed venous blood temperature response to exercise in heart failure patients treated with short–term vasodilators. Clin Physiol 1985; 5:503–14.

Teerlink Jr, Jalaluddin M, Anderson S, et al. Ambulatory ventricular arrhythmias in patients with heart failure do not specifically predict an increased risk of sudden death. PROMISE (Prospective Randomized Milrinone Survival Evaluation) Investigators. Circulation 2000; 101:40–6.

Vasan RS, Larson MG, Benjamin EJ, Evans JC, Reiss CK, Levy D. Congestive heart failure in subjects with normal versus reduced left ventricular ejection fraction: prevalence and mortality in a population–based cohort. J Am Coll Cardiol 1999; 33:1948–55.

Vranckx P, Van Cleemput J. Prognostic assessment of end–stage cardiac failure. Acta Cardiol 1998; 53:121–5.

Willenheimer R, Erhardt LR. Value of 6–min–walk test for assessment of severity and prognosis of heart failure. Lancet 2000; 355:515–6.

(List continued on next page.)

*Primary Examiner*—Max Hindenburg
(74) *Attorney, Agent, or Firm*—Tim L. Burgess

(57) ABSTRACT

Methods of predicting mortality or imminent death in patients with congestive heart failure include detecting changes in the patient's temperature and/or the detection of hypothermia. The invention also relates to devices and kits for implementation of these methods.

31 Claims, 8 Drawing Sheets

HYPOTHERMIA PREDICTS SHORT SURVIVAL IN PATIENTS WITH CHF

OTHER PUBLICATIONS

Hunt AA. Current status of cardiac transplantation. Jama 1998; 280: 1692–8.

Rouleau J, Shenasa M, De Champlain J, Nadeau R. Predictors of survival and sudden death in patients with stable severe congestive heart failure due to ischemic and nonischemic causes: a prospective long term study of 200 patients. Can J Cardiol 1990; 6:453–60.

Siddiqui, H, Patel, S, Lai, BN, Nagavi, H, Hypothermia: A New Indicator of Imminent Death in Congestive Heart Failure, J Amer Coll Cardiology, 33:2:2A Feb. 1999.

Adams KF, Jr., Sueta CA, Gheorghiade M, et al. Gender differences in survival in advanced heart failure. Insights from the First study. Circulation 1999; 99:1816–21.

Anker SD, Ponikowski P, Varney S, et al. Wasting as independent risk factor for mortality in chronic heart failure [published erratum appears in Lancet 1997 Apr. 26;349(9060)::1258]. Lancet 1997; 349:1050–3.

Bonaduce D, Petrett A M, Marciano F, et al. Independent and incremental prognostic value of heart rate variability in patients with chronic heart failure. Am Heart J 1999; 138:273–84.

Cohn JN, Rector TS. Prognosis of congestive heart failure and predictors of mortality. Am J Cardiol 1988; 62:25A–30A.

Doval HC, Nul DR, Grancelli HO, et al. Nonsustained ventricular tachycardia in severe heart failure. Independent marker of increased mortality due to sudden death.GESICA–GEM Investigators [see comments]. Circulation 1996; 94:3198–203.

Fox E, Landrum–McNiff K, Zhong Z, Dawson NV, Wu AW, Lynn J. Evaluation of prognostic criteria for determining hospice eligibility in patients with advanced lung, heart, or liver disease. Support Investigators. Study to Understand Prognoses and Preferences for Outcomes and Risks of Treatments [see comments]. Jama 1999; 282:1638–4.

Ho KK, Moody GB, Peng CK, et al. Predicting survival in heart failure case and control subjects by use of fully automated methods for deriving nonlinear and conventinal indices of heart rate dynamics. Circulation 1997; 96:842–8.

Myers J, Gullestad L, Vagelos R, et al. "Clinical, hemodynamic, and cardiopulmonary exercise test determinants of survival in patients referred for evaluation of heart failure." Ann Intern Med 1998; 129:286–93.

Ommen SR, Hodge DO, Rodeheffer RJ, McGregor CG, Thomson SP, Gibbons RJ. Predictive power of the relative lymphocyte concentration in patients with advanced heart failure [see comments]. Circulation 1998; 97:19–22.

Parameshwar J, Keegan J, Sparrow J, Sutton GC, Poole–Wilson PA. Predictors of prognosis in severe chronic heart failure. Am Heart J 1992; 123:421–6.

METHOD AND APPARATUS FOR PREDICTING MORTALITY IN CONGESTIVE HEART FAILURE PATIENTS

CROSS-REFERENCE TO RELATED APPLICATION

The present application claims the benefit of 35 U.S.C. 111(b) Provisional Application Ser. No. 60/123,342 filed Mar. 8, 1999 and entitled "Method of Predicting Mortality in Congestive Heart Failure Patients.

BACKGROUND OF THE INVENTION

1. Field of the Invention

The present invention generally relates to methods of predicting mortality in patients with congestive heart failure, and more particularly to such methods including detection of hypothermia in a congestive heart failure patient. The invention also relates to apparatus, devices and kits for carrying out the methods.

2. Description of the Background Art

Congestive heart failure (CHF) is a leading, and increasing, cause of morbidity and mortality. Numerous predictors of mortality in patients with CHF have been described in the literature. For example, Myers et al.[1] reports that in predicting outcome in severe chronic heart failure, peak oxygen uptake ($VO_2$) surpassed clinical variables, right-heart catheterization data, exercise time, and other exercise test variables. Other prognostic variables have also been identified, including left ventricular ejection function (LVEF), age, creatinine, right ventricular ejection fraction (RVEF), hyponatremia, bilirubin and recently, lymphocyte count. Nevertheless, these variables together account for only a portion of the variance, with the strong predictors usually applying to only a few patients, leaving prognosis uncertain for the individual patient. The ability to accurately predict which patients are likely to have the shortest survival times is particularly needed in the selection of patients for heart transplantation or left ventricular assist device (LVAD) implantation. [2-19]. An accurate prognosis helps physicians optimize therapies for their patients. Even if in the circumstances a more accurate prognosis would not improve therapy (e.g., when the therapy has already been optimized), most patients and their families want as accurate a prognosis as possible.

SUMMARY OF THE INVENTION

The invention contemplates a method, apparatus and kit devices for detecting a drop in a patient's body temperature as a means of predicting imminent death in congestive heart failure patients.

In accordance with this invention, a method of monitoring a patient with congestive heart failure for prognosis of survival comprises: obtaining an initial body temperature which is not elevated above normal, then obtaining subsequent body temperatures of the patient and determining whether the subsequent temperatures fit any of predetermined criteria showing a condition of congestive heart failure hypothermia. A method of warning of imminent mortality in a patient suffering from congestive heart failure absent therapeutic intervention comprises sensing internal and/or external temperatures of a patient, analyzing the temperatures to determine a data set conforming to a predefined condition signifying congestive heart failure hypothermia; and issuing an alarm reporting said condition.

Such criteria include any one or more of: (i) a decrease in temperature of about 2° F. or more from said initial temperature, (ii) a decrease in temperature of 1° F. or more within a 12 hour period, (iii) a decrease in temperature of about 1° F. or more over 24 hours if the patient's mean temperature is at or below 96.5° F., and (iv) a decrease in mean temperature of two standard deviations below the patient's mean temperature over the prior 24 hours.

An embodiment of the method of the invention involving a graded or two-step manner of monitoring for risk of imminent mortality in a patient suffering from congestive heart failure, comprises (a) determining an initial body temperature which is not in excess of 97° F., (b) obtaining subsequent body temperatures of the patient and determining whether the subsequent temperatures fit any of a first set of predetermined criteria for a condition of developing congestive heart failure hypothermia, and if so, (c) monitoring the patient under a second set of predetermined criteria for a developed condition of congestive heart failure hypothermia and determining whether the subsequent temperatures fit any of said second set of predetermined criteria, and if so; (d) triggering an alarm for intensive therapy.

A preferred embodiment measures the patient's temperature at more than one site, analyzes the detected temperatures and triggers an alarm should a temperature decline be detected. In a particular of this method, the temperature gradient between the patient's core and body surface is measured. In accordance therewith, a preferred method of the invention comprises (a) determining an initial body temperature which is not in excess of 97° F., (b) obtaining at least one temperature sensor for measuring a cutaneous body temperature and at least one sensor for measuring a core body temperature; (c) positioning said sensors to be in direct contact with a patient having said initial temperature; (d) transmitting said core body temperature and said cutaneous body temperature at predetermined timed intervals to a processor programmed to analyze said temperatures; (e) analyzing said core body temperature and said cutaneous body temperature to determine if said temperatures fall outside of a predetermined criteria for a decrease in the patient's temperature signifying a condition of congestive heart failure hypothermia; and (f) triggering an alarm if said temperatures fall outside of said predetermined criteria.

In one aspect the invention includes a method of monitoring a patient with congestive heart failure for prognosis of time remaining to death absent intervention, by obtaining an initial body temperature which is not elevated above normal, obtaining subsequent body temperatures of the patient and determining whether the subsequent temperatures fit any of predetermined criteria showing a condition of congestive heart failure hypothermia, and if so, predicting time to death according to the formula: time to death (hours)=12.5 (° F. −95.24), where ° F. represents the current temperature of the patient.

The invention embodies apparatus, kits and temperature sensor devices for implementation of the invention. One such implement analyzes temperature measurements and comprises a processor programmed to activate an alarm if a temperature gradient between a core body temperature and a surface body temperature exceeds a predetermined criteria determined to signify congestive heart failure hypothermia.

A device useful in the present invention for monitoring body temperature preferably includes a temperature sensor for monitoring the core body temperature of the patient. Another useful temperature sensor comprises a temperature measuring device having means for notifying a patient diagnosed with congestive heart failure when the patient's temperature decreases below a predetermined criteria.

In a greater particular, an apparatus useful in the practice of the invention includes a temperature detector for sensing temperature of a patient and generating a signal representative of the sensed temperature, a mount of said temperature sensor for indwelling or external placement on the patient, a data recorder for receiving said detector signals at timed intervals and using the signals to produce and store data representing temperatures of the patient sensed over time, an analyzer for processing said stored data to determine a data set conforming to a predefined condition signifying congestive heart failure hypothermia and outputting a signal indicative of the condition, and an alarm for receiving and reporting said output signal indicative of said condition. The apparatus can also include means of furnishing therapeutic warming to the patient.

It is further useful for the apparatus to include means providing one or more additional predictors including one or more of $O_2$ saturation, $P_ACO_2$, pH, respiratory rate, QRS width, R-R variability and T wave alternans, heart rate, blood pressure, pulse pressure and dP/dt, as a composite index to maximize sensitivity and specificity. Because most patients experience a fall in cardiac output and blood pressure before death (e.g. patients without known heart disease who are dying of sepsis, stroke, trauma, or failure of the kidneys, liver, or respiratory system) a temperature monitoring apparatus of the present invention augmented by e monitoring devices of the latter type also serves to warn of a risk of imminent death in these latter patients.

Yet another embodiment of the invention is a kit comprising a device having at least one temperature sensor for transmitting a signal indicative of the temperature of a patient with congestive heart failure, the means of receiving the signal indicative of the temperature of a patient and analyzing such signal to determine whenever the patient experiences a decline in temperature outside of a predetermined normal range, and a means for triggering an alarm if such a temperature decline occurs.

BRIEF DESCRIPTION OF THE DRAWINGS

The accompanying drawings, which are incorporated in and form a part of the specification, illustrate the embodiments of the present invention, and with the description, serve to explain the principles of the invention. In the drawings.

Figure 1:
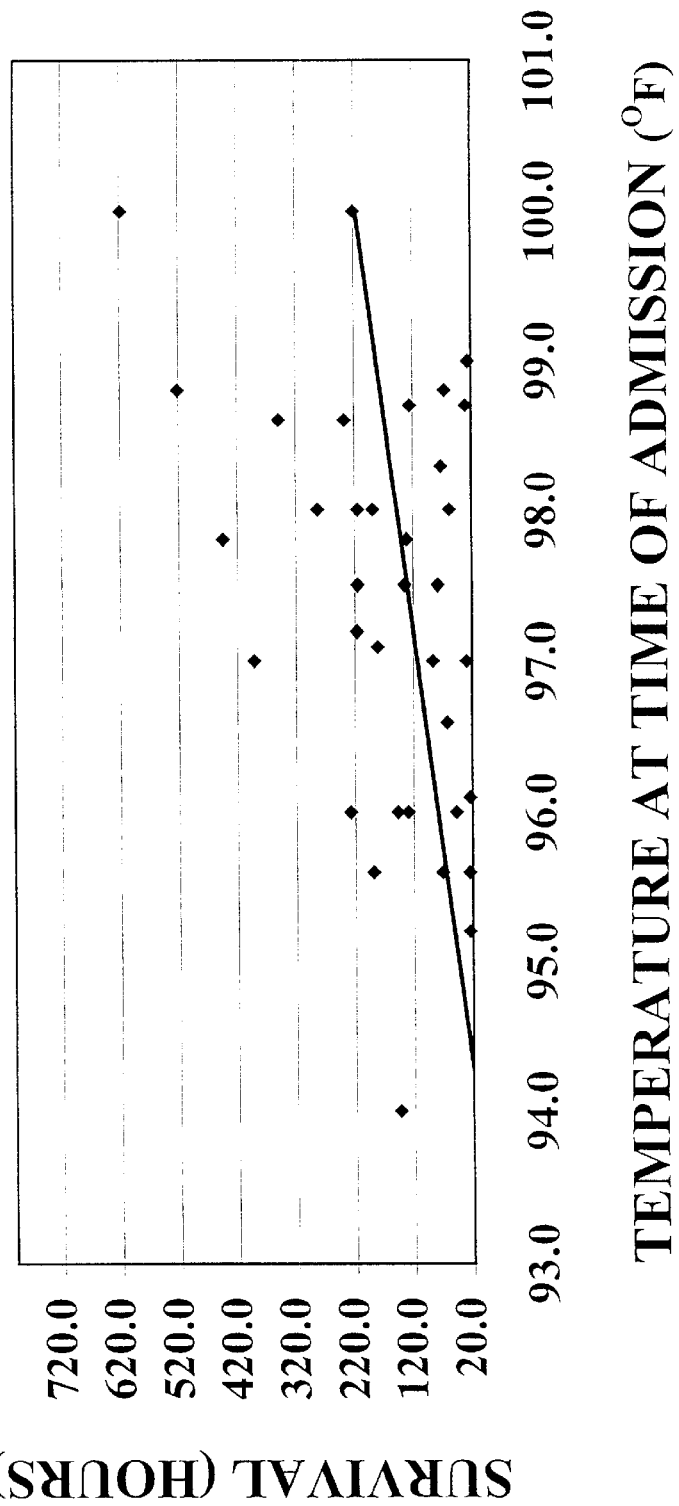
FIG. 1 is a graph illustrating that the temperature of a congestive heart failure patient upon admission into the hospital is predictive of that patient's survival.

It is to be noted that the drawings illustrate only typical embodiments of the invention and are therefore not to be considered limiting of its scope, for the invention admits to other equally effective embodiments.

DETAILED DESCRIPTION OF PREFERRED EMBODIMENTS

A. Discovery: Hypothermia Is An Indicator of Imminent Death in Congestive Heart Failure Initially, it was observed that one patient's temperature (T) fell from 97° F. to 91.7° F. two hours prior to death from severe congestive heart failure (CHF) despite maintenance of normal heart rate, blood pressure and mentation. A similar situation was noted in two more patients. In the third patient, medical treatment (nitrates, enalapril, digoxin) was intensified, the patient was warm, and the patient survived. This led to the novel hypothesis that some patients become hypothermic prior to death from congestive heart failure. This hypothesis is in contrast to teachings in the field suggesting that CHF is characterized by normal and slightly elevated temperatures.

Hypothermia was investigated as an indicator of imminent death from congestive heart failure. The outcomes of a number of patients admitted to the hospital with a diagnosis of congestive heart failure (CHF) were investigated to correlate their body temperature with death.

Hypothermia is generally defined as a core body temperature of 35° C. (95° F.) or below and is classified as mild (35–32° C.), moderate (<32 to 28° C.), or severe (<28° C.). See Petty, K. J. "Hypothermia" in *Cardinal Manifestations and Presentation of Diseases*, McGraw-Hill Companies, 1998.

The Department of Medical Records at Hermann Hospital in Houston, Texas, USA, was the source of the data reported herein. A case-control retrospective study of patients who were admitted with CHF as one of the principal diagnoses was performed. The diagnosis was in accordance with the International Classification of Diseases, 9th Revision, Clinical modification (ICD-9 CM). Information about CHF admissions, deaths and discharges between Jan. 1, 1996 till Jun. 1, 1998 was collected.

The cases were selected on the basis of having pure CHF without any other condition known to affect temperature. Exclusion criteria included all the deaths and discharges that were complicated with temperature confounders such as hepatic failure, infections, acute stroke, sepsis, thyroid disease, alcohol intoxication, exposure to cold or heating blankets. Medications were not causes for exclusion (aspirin, non-steroidal anti-inflammatory drugs, acetaminophens, steroids, vasopressors). Cardiovascular diseases were not causes for exclusion either.

Patients who died were selected as cases and were divided into two groups; those who died with hypothermia and those who died without it. Controls were randomly selected patients discharged alive with CHF as a primary diagnosis who fulfilled the same inclusion criteria as the cases. Controls were divided into two groups in a manner identical to the cases (i.e., those having hypothermia and those without hypothermia). Overall 148 patients (53 cases and 95 controls) were analyzed by SPSS software (1998).

TABLE 1

UNIVARIATE ANALYSIS

| VARIABLES | CASES (N = 53) | CONTROLS (N = 96) | P VALUE |
|---|---|---|---|
| Age (Years) | 73.45 +/− 13.8 | 69.3 +/− 14.3 | 0.088 |
| Sex (M:F) | 24:29 | 52:44 | |
| Race (W,B,O) | W:29, B:19, O:05 | W:41, B:46, O:4, H:5 | |
| Systolic BP | 118.4 +/− 28.1 | 136.9 +/− 26.7 | .0001 |
| Diastolic BP | 70 +/− 17.5 | 75.7 +/− 17.5 | .060 |
| HR | 88.1 +/− 21.9 | 84.6 +/− 19.9 | .320 |
| Creatinine (Cr) | 1.9 +/− 1.4 | 1.4 +/− 1.1 | .014 |
| Sodium (Na) | 137.9 +/− 3 | 138 +/− 3.2 | .941 |
| LVEF (%) | 37 +/− 17.7 | 42.4 +/− 14.9 | .364 |
| RVF | ↓↓ | ↓ | |
| Leukocytes (WBCs) | 8.8 +/− 2.1 | 8.1 +/− 1.8 | 0.022 |
| Lymphocyte Count | 15 +/− 6.8 | 20.1 +/− 9.3 | .001 |
| Last Temp (T2) | 96.5 +/− 2.3 | 97.6 +/− 0.9 | .0001 |
| Adm. Temp (T1) | 97.2 +/− 1.8 | 97.7 +/− 0.8 | .025 |
| Ave. Temp | 97.1 +/− 1.5 | 97.6 +/− 0.7 | .003 |
| T↓(last 12 hrs) | −0.6 +/− 1.9 | −0.01 +/− 1.0 | .009 |
| ΔT (T2-T1) | −0.7 +/− 2.7 | −0.1 +/− 1.1 | .066 |

Table 1 gives patient demographics of cases (deaths) and controls (patients discharged alive with CHF) and univariate analysis of differences (2 tailed P; equal variances assumed). Patients who died of CHF had lower systolic blood pressure, serum sodium, leukocyte count and higher creatinine. Age and diastolic blood pressure were borderline predictors. The most significant predictors were the last recorded oral temperature, lymphocyte count, temperature fall over the last 12 hours, average temperature and admission temperature.

TABLE 2

MULTIVARIATE LOGISTIC REGRESSION ANALYSIS

| VARIABLE | ODDS RATIO | 95% CI | P |
|---|---|---|---|
| Systolic Blood Pressure | 0.972 | 0.94–0.99 | 0.042 |
| Diastolic Blood Pressure | 1.023 | 0.98–1.06 | 0.247 |
| Creatinine | 1.570 | 1.10–2.23 | 0.011 |
| Leukocytes | 1.343 | 1.04–1.71 | 0.019 |
| Lymphocyte Count | 0.920 | 0.86–0.97 | 0.005 |
| Last Temp | 10.254 | 3.74–28.10 | 0.00001 |

Table 2 gives the multivariate logistic regression analysis of variables of systolic blood pressure (SBP), creatinine (CR), leukocyte count (WBC), lymphocyte count (lymph), last temperature (temp, indicating the last recorded temperature divided categorically into ≧97° F. and <97° F.) and diastolic blood pressure (DBP). Variables with a P value above 0.1 in the univariate analysis were not included. The odds ratio and 95% confidence intervals are shown. The strongest predictor of death during the patient's hospital stay was the last recorded oral temperature, followed by the lymphocyte count. In this case-control study, hypothermia emerged as a strong predictor of death in patients admitted with congestive heart failure.

This was surprising because temperature is not listed as a prognostic variable in any of the dozen of papers prognosis of CHF. Indeed, it was not even been included in the data sets. Nor is CHF listed as a cause of hypothermia though age, stroke, medications and shock which often coexists with CHF are known risks for hypothermia. Therefore, we undertook a second study to see if the first could be confirmed.

Because case-control studies have well-known limitations, including missing data and can be confounded by unsuspected associations, a second type of study was performed, a retrospective cohort study. All of the 1998 admissions to Hermann Hospital whose primary discharge diagnosis (or death) was congestive heart failure were analyzed, using the same International Classification of Disease coding as in the previous study. For patients admitted more than once during the year, only the last admission was studied. Potential confounders of temperature, such as sepsis, acute stroke, thyroid disease, alcohol intoxication or cold exposure, resulted in the exclusion of 35 of the original 423 patients; medications were not used to exclude patients. Another 97 were excluded because of multiple admissions to the hospital during that year. Medications were not cause for exclusion. The remaining 291 charts were reviewed according to the following prospective criteria, which include the reported prognostic variables for CHF, in groupings that conform to the usual stages of clinical assessment of the patient. Analsis was by Cox regression [22,23].

Bedside variables were considered first. These included age, sex, a history of hypertension or diabetes or coronary artery disease or symptoms thereof, New York Heart Association (NYHA) CHF class, valvular disease, heart rate, blood pressure and temperature.

In situations of missing data, the variable was dropped if more than a third of the patients were lacking that particular variable. Of the remaining variables, missing data were handled by assuming the mean of the cohort for that particular variable.

A second analysis examined the prognostic ability of admission temperature compared to arrhythmia (ventricular tachycardia and/or atrial fibrillation) and RR variability. No analysis for T-wave alternans was undertaken because arrhythmic death was not the focus of the study.

A third analysis compared temperature to echocardiographic and angiographic variables.

A fourth analysis compared temperature to laboratory variables, including creatinine, serum sodium, lymphocyte count, glucose, potassium and carbon dioxide.

In the comparison of bedside variables (shown in Table 5), hypothermia was the best predictor of in-hospital mortality (P=0.004), followed by systolic blood pressure (P=0.015) NYHA class (P=0.47) and female sex (P=0.047). Tricuspid regurgitation showed a trend toward significance (P=0.06), but hypertension, diabetes, coronary artery disease, diastolic BP, mitral regurgitation and heart rate on admission did not.

TABLE 5

Multivariate analysis of bedside variables (derived from history and exam) predicting in-hospital mortality of CHF patients. Temperature is mean of hospital stay; NYHA = New York Heart Association; CHF = Congestive Heart Failure: TR = Tricuspid valve regurgitation; SBP = Systolic Blood Pressure on admission. Variables not associated with mortality were age, history of hypertension, diabetes, or coronary atherosclerosis; findings of aortic or mitral valve disease, heart rate, and diastolic blood pressure.

| Variable | Odds Ratio | P Value |
|---|---|---|
| Temperature | 0.3296 | 0.0042 |
| Sex (Female) | 3.6733 | 0.0468 |
| NYHA | 2.3920 | 0.0469 |
| TR | 31.6312 | 0.0604 |
| SBP | 0.9561 | 0.0154 |

Compared to electrocardiographic variables, such as arrhythmia and variability in the RR interval (P=0.88 and 0.89, respectively), temperature was more significant, with a borderline P value of 0.06. Most charts locked on LVEF or RV dimension for that specific hospitalization. Analysis of just those cases that did have the data revealed that, compared to LVEF, temperature was of borderline significance (OR=0.45, P=0.06) while LVEF was not a significant predictor (P=0.77). However, among cases with data on RV enlargement (OR=8.8, p=0.014), temperature lost predictive value. This must be interpreted with caution because it is a subset analysis (only 2 variables) on a subset of patients (96 of 291) that may have a selection bias. In any event RV function can not be evaluated at the bedside or monitored non-invasively.

Compared to laboratory variables, temperature was of borderline significance (P=0.077), and creatinine, a well-recognized prognostic factor, was the most significant, with a P value of 0.003. In this data set, hyponatremia and lymphopenia were not significant (P=0.53 and P=0.70, respectively). Bilirubin, a recently described predictor, was not measured in enough patients to be included in the multivariate analysis. In a subset analysis of 193 patients, T remained predictive (OR =0.32, P=0.0008) but bilirubin (P=0.27) was not.

Other variables with too many missing data points for inclusion in the multivariate analysis, which were compared in subset analyses to temperature were VT(OR=8.7,p= 0.0000, vs OR=0.44, p=0.046 for T) and variables which did not predict mortality (AF,R-R variability, and use of beta-blockers, ACE inhibitors, aspirin, or amiodarone) though in each comparison T remained significantly and inversely associated with mortality.

Taken together, these different analyses of different data sets demonstrate with considerable consistency an association of hypothermia with CHF mortality. Hence, the data presented in the present application, derived from two different types of analysis, are robust. Indeed it is likely that standardizing the T data, i.e., per rectum, aural, or oral, etc., normalizing to correct for circadian variation, and collecting continuous T, will increase the sensitivity and specificity of T as a prognostic variable.

Temperature, shown in Table 1 with a P value of 0.025, was also shown to correlate with survival. FIG. 1 plots the temperature at the time of admission against the survival time of the patient in hours. As can be seen in the graph shown in FIG. 1, temperature at the time of admission is related to the patient's survival time. Moreover, a core temperature decrease from the patient's baseline temperature (e.g., average temperature or temperature upon admission to the hospital) is predictive of imminent death in the patient (i.e., within 24 hours) and suggests that the patient needs more intensive medical therapy or consideration for heart transplantation or left ventricular assistance.

Figure 5:
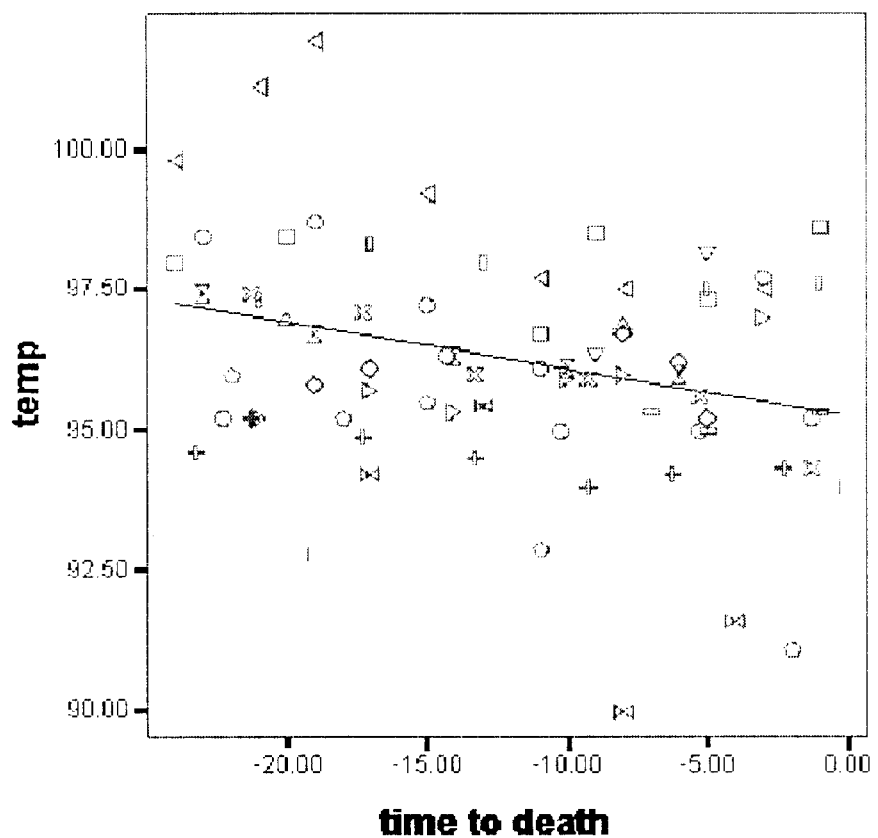
FIG. 5 is a graph illustrating a time to death calculation in hypothermic congestive heart patients.
Figure 6:
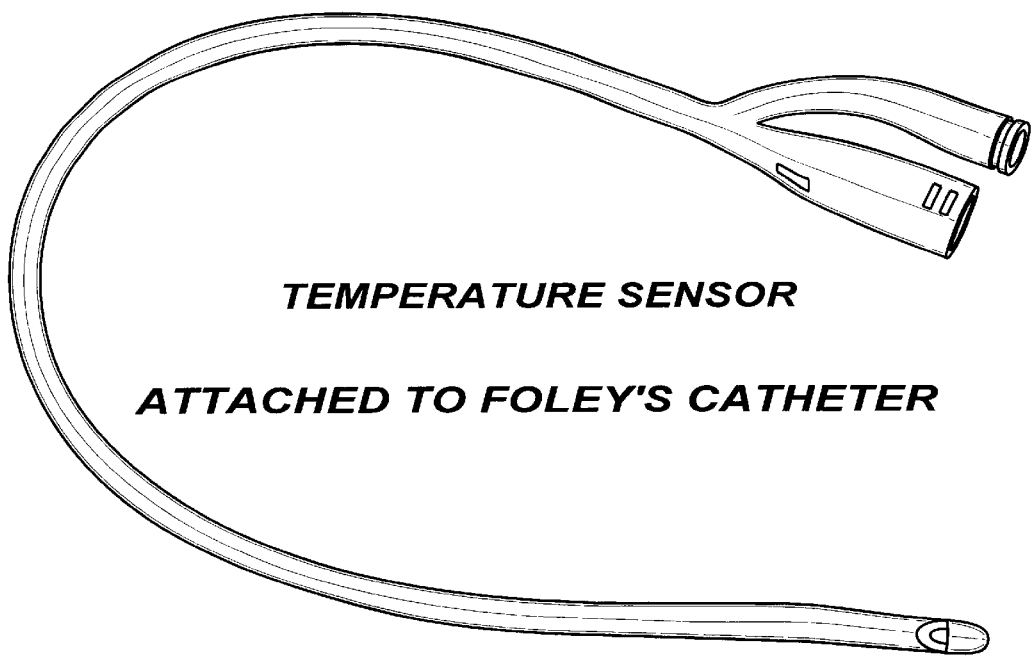
FIG. 6 is a depiction of an indwelling temperature sensing device suitable for use in the invention.
Figure 7:
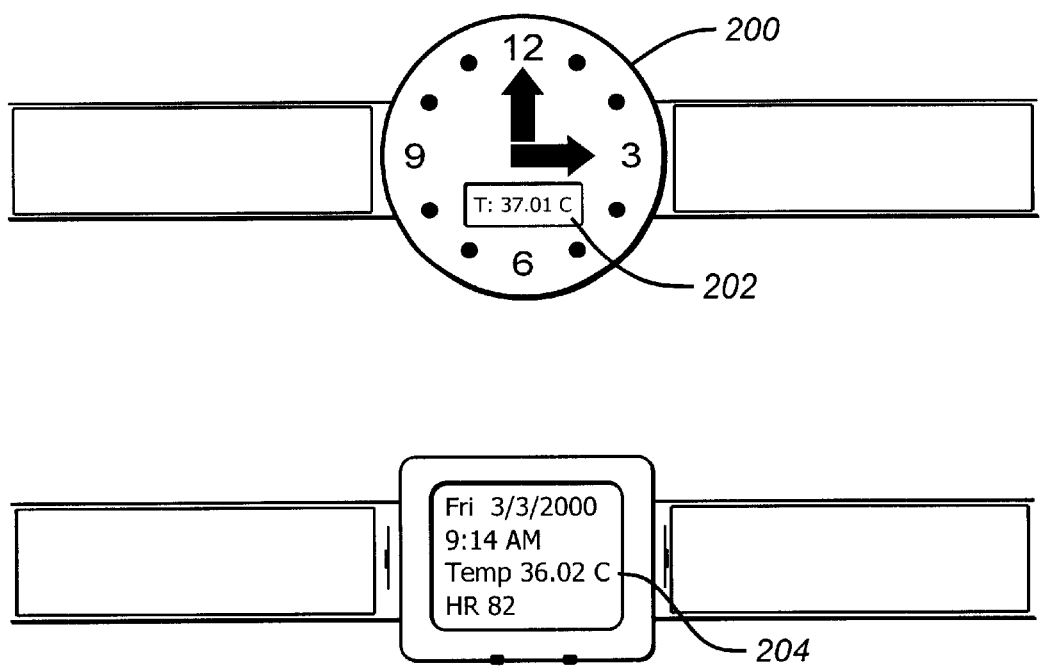
FIG. 7 is a depiction of a temperature sensing device wearable by a patient for remote signaling of an alarm of a hypothermic condition in accordance with the invention.
Figure 8:
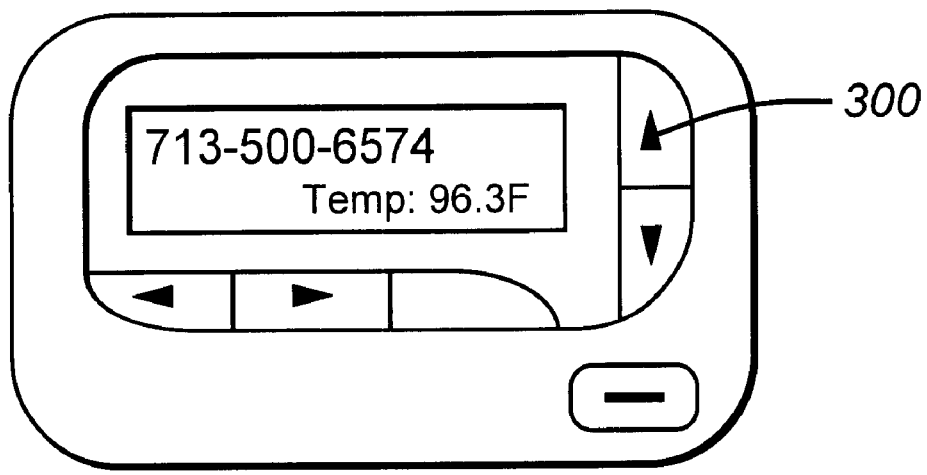
FIG. 8 is a depiction of a temperature sensing device attached to a pager for remote signaling of an alarm of a hypothermic condition in accordance with the invention.

A regression analysis of the data shown in FIG. 1 produces the graph illustrated in FIG. 5, which yields the formula for time to death once hypothermia commences in a congestive heart failure patient.

The literature suggests that several competing mechanisms may be operating in the observed temperature decrease. Factors that are expected to increase temperature in congestive heart failure, as noted in prior reports, are listed in Table 3. These reports also suggest that a number of factors may contribute to the decrease in temperature in patients with congestive heart failure, as listed in Table 4.

TABLE 3

FACTORS THAT MAY DECREASE TEMPERATURE IN CHF

Vasodilator therapy
Inactivity
Decreased metabolism due to hypoxemia and severe vasoconstriction
Decreased liver/intestinal metabolism due to venous congestion
Anti-inflammatory effect of hypercortisolemia
Malnutrition
Cell senescence
Down regulation of mitochondrial uncoupling proteins
Down regulation of adenylate cyclase
Down regulation of β adrenergic receptors
Decreased metabolism due to CNS effects of norepinephrine, epinephrine, angiotensin II
Uncoupling of receptors from G proteins
Increased neurotensin

TABLE 4

FACTORS THAT MAY INCREASE TEMPERATURE IN CHF

Figure 2:
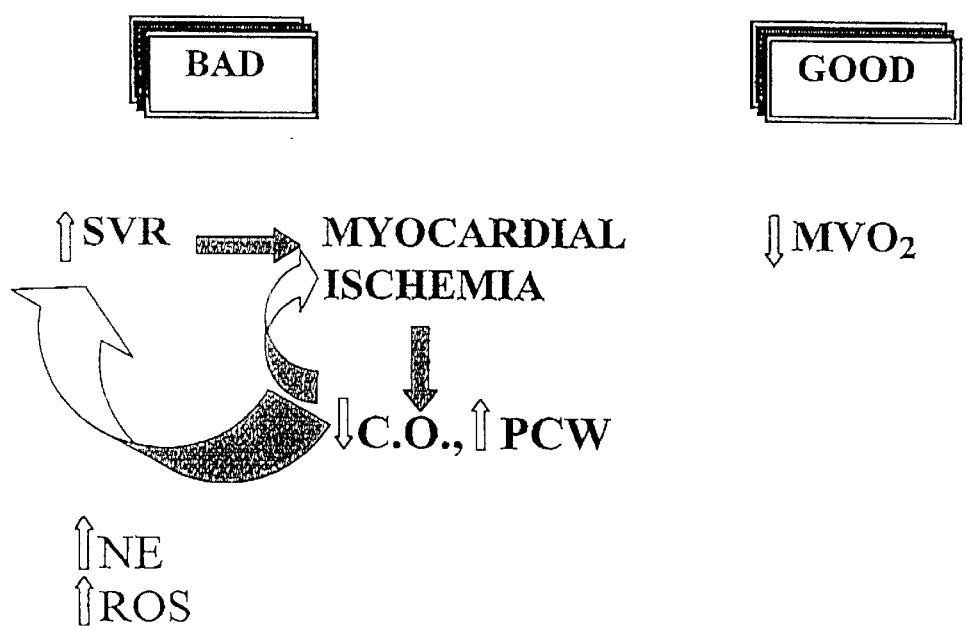
FIG. 2 illustrates the consequences of hypothermia in a congestive heart failure patient.

Tachycardia
Tachypnea
Vasoconstriction
"Oxygen-wasting" effect of norepinephrine, epinephrine
$B_3$ adrenergic stimulation
Pyrogenic cytokines (interleukins no 1, 6, 8 and TNF-α)
Oxidation by myocardial macrophages
Increased adrenergic receptors due to increased cortisol B. Consequences of Hypothermia in CHF It is not known whether hypothermia adds to a patient's risk of death or whether it is solely a marker of imminent death. The excess vasoconstriction caused by hypothermia may initiate local tissue death, hepatic congestion or a hypothalamic effect. As shown in FIG. 2, hypothermia causes an increase in systemic vascular resistance (SVR), which can precipitate or complicate the symptoms of myocardial infarction such as decreased cardiac output (C.O.) and increased pulmonary capillary wedge pressure (PCW). Such effects are known to increase the levels of norepinephrine (NE), angiotensin II (AII), epinephrine (EP), central nervous tissue (CNS), interleukin (IL), tumor necrosis factor (TNF) and the production of reactive oxygen species (ROS). Hypothermia also decreases the myocardial oxygen consumption ($MVO_2$).

The inventors propose that the reasons that some of the CHF patients develop hypothermia at the very end stage of their disease include a decline in heat production due to adrenergic receptor uncoupling, inactivity, anorexia, hypoxemia, and other factors (see Table 3).

In addition, since stable CHF patients have relatively higher resting basal metabolic rates and oxidative stress (see Table 4), the bodies of these patients may well use an inefficient f oxidative pathway (such as glycolysis). Increased lactate level is another indicator that these patients are not using oxygen efficiently. This evidence, considered in light of Shellock et al. [20,21] regarding the effects of vasodilators and the core temperature decrease with exercise in heart-failure patients, strongly suggests that in pre-terminal CHF there is decompensation of sympathetic constriction of the peripheral vascular bed. Little by little the warm core blood circulates into cool extremities and muscles resulting in a drop in core temperature. By comparing the peripheral cutaneous temperatures of hypothermic and normothermic patients, it can be determined whether there is relatively more peripheral vasodilation in congestive heart failure patients. A suitable parameter for comparison is the gradient of temperature between peripheral and core areas in the two groups.

Thus, a core temperature decrease from the patient's baseline temperature (e.g., average temperature or temperature upon admission to the hospital) is predictive of imminent death in the patient (i.e., within 24 hours) and suggests a need for intensive medical therapy or consideration for heart transplantation or left ventricular assistance. In addition to the successful intervention in one patient described above, the complications of vasoconstriction caused by cold suggest that hypothermia may not only be a prognostic marker and a stimulus to intervene with medicines, devices or transplantation, but also an indication to warm the patient, indeed a recent paper described an improvement in symptom when CHF patients (who were not hypothermic) were warmed. These findings differ from the medical literature in that:
1) Very mild hypothermia, such as was observed in terminal CHF patients, has not been associated with increased mortality (perhaps because most of the patients in those hypothermia reports did not have CHF).
2) Warming did not just relieve symptoms and signs of CHF but also prolonged life.

C. Identifying Patients at Risk of Imminent Death from Congestive Heart Failure

Hypothermia, as shown above, is a clinically significant sign that a patient needs more intensive medical therapy or consideration for heart transplantation or left ventricular assistance.

One embodiment of the present invention provides one or more sensors that patients diagnosed with CHF can wear at home to warn them or their caretakers when they need to call their physician or go to the hospital for observation and/or treatment. The sensors may be fiber or plastic strips containing thermosensitive chromophores or liquid crystals, similar to conventional fever strips used in the home for measuring a child's temperature. Any suitable temperature measuring device, such as a remotely monitored thermistor or thermocouple assembly, could be substituted. Such sensors may be skin electrodes that are taped onto the body, strapped onto the body, or built into clothing or accessories that are worn by the patient. For example, a temperature sensor may be built into a hearing aid or eyeglasses for those patients that wear one or the other. In addition, wristwatches, beepers, caps, belts, underwear, socks, shoes, rings, necklaces and other types of clothing or clothing accessories may be adapted to measure body temperature.

Figure 3:
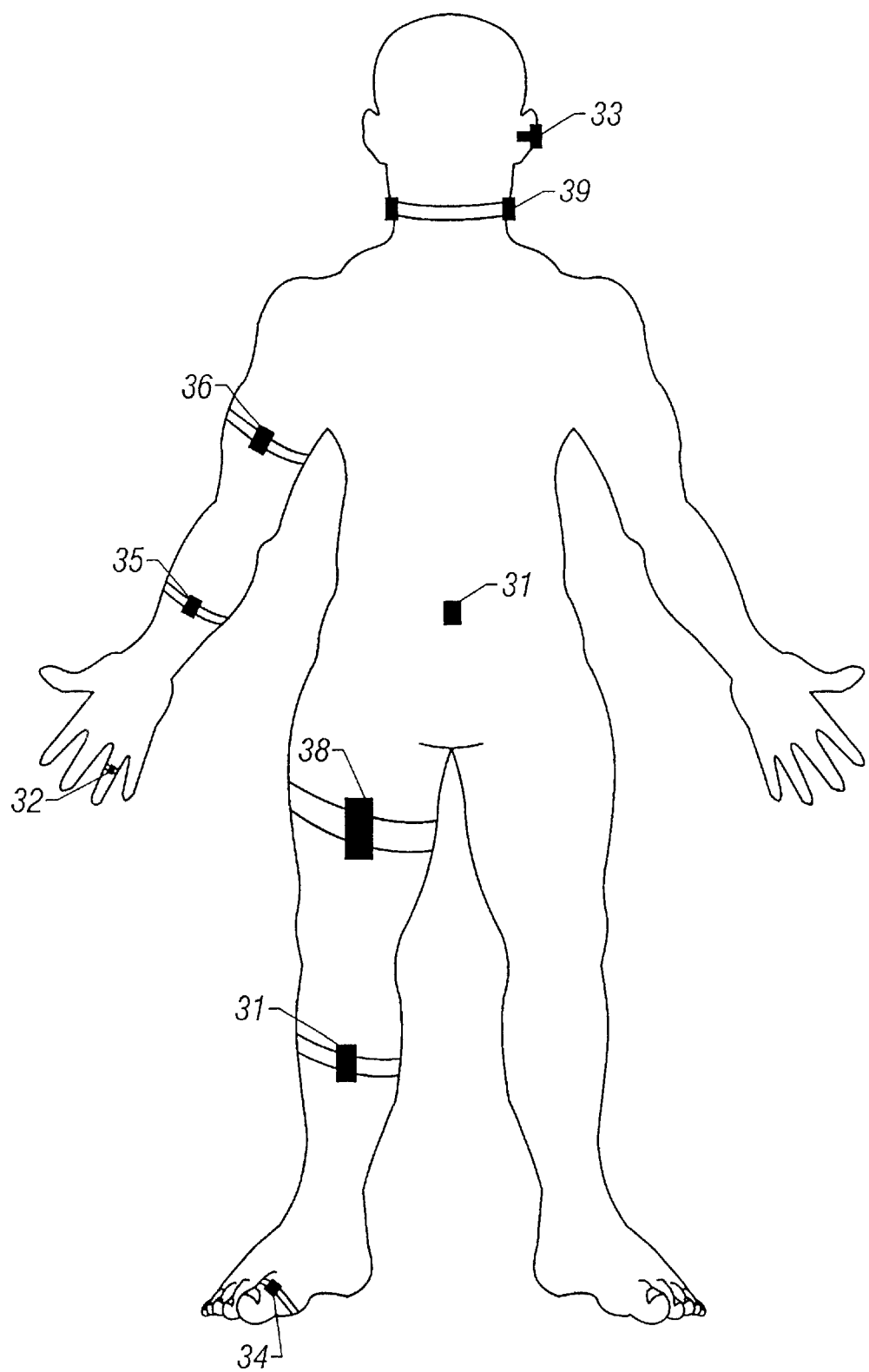
FIG. 3 represents an embodiment of placement of cutaneous/core temperature monitoring devices, e.g., a Foley catheter, a wrist watch or a beeper.

Another embodiment of the present invention provides multiple sensors for the measurement of cutaneous and core temperatures of a patient. The placement of temperature sensors at any or all of the locations shown in FIG. 3 is envisioned. In addition, bilateral temperature sensors may be placed on each leg and each arm. One or more cutaneous sites, such as fingers 32, toes 34, upper arms 36, thighs 38 and neck 39 are monitored. Additional sites such as the upper arm 36 and the lower leg 37 may also be monitored. Each strip is not necessarily connected to another, and may be monitored separately or simultaneously.

The patient is preferably scored on his overall temperature compared to a general reference criteria, or the patient's own reference criteria if known. Additionally, or alternatively, the pattern of heat distribution over the body, reflecting variations in vasoconstriction, can be considered against reference data for each respective point. Although the lability in temperature is also likely to predict death because it is a sign of autonomic dysfunction, the devices described herein are disclosed for use in monitoring CHF patients, these devices may also be used in a number of other situations such as monitoring peripheral vascular circulation.

Temperature sensors can be directly attached to or inserted into any medical device that comes into direct contact with the patient such as a nasogastric tubes, Dobbhoff and endotracheal tubes, pulmonary artery catheters (e.g., Swan-Ganz catheter), urinary catheters, T-tubes, drains, rectal tubes, arterial lines, triple-lumen and dialysis catheters, pacemakers (both temporary and permanent), intra-aortic balloon pumps, implantable defibrillators, remote (EGIR) monitors, Hickman and similar chronic infusion catheters, pulse oximetry probes, nasal probes for carbon dioxide monitoring, intravenous needles, and other invasive devices. Such indwelling or attached devices preferably include on the instrument a thermistor or thermocouple device to remotely monitor the core temperature of the patient. The core temperature may also be monitored by any suitable non-invasive technique, such as by placement of a sensor in the umbilicus 31 or ear 33.

Cutaneous temperature measurements can be taken by including temperature sensors in skin electrodes, casts, hearing aids, and the like.

D. Patient Monitoring

Whenever a patient diagnosed with CHF is admitted to a hospital, the patient's temperature is taken. If the patient's admitting temperature is less than about 96.5° F., the patient is identified as a candidate for constant temperature monitoring.

Figure 4:
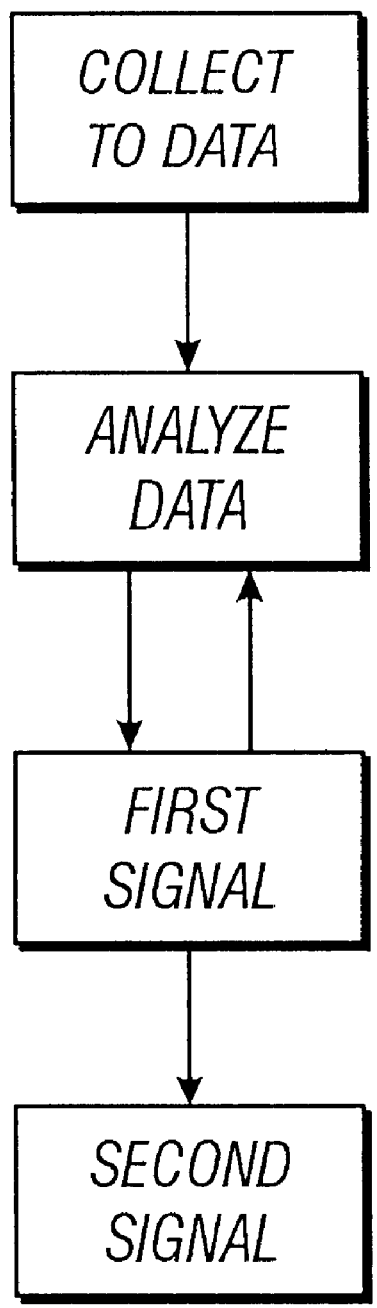
FIG. 4 is a schematic of one embodiment of a staged or two step process of identifying patients at risk of imminent death.

A process of patient temperature monitoring is illustrated in FIG. 4. At least one, and preferably multiple temperature sensors, are put into place. The data collected from these temperature monitors is analyzed. Preferably the data is digitized and transmitted to a processor programmed to compare the temperature data to the patient's reference data. The data can be compared as a whole, or it can be compared for each temperature sensor in place.

The temperature detected by the temperature sensor is analyzed at predetermined time intervals, or averaged over specific time intervals and then the average analyzed. The temperature measurements are analyzed to detect deviations from the patient's baseline information and the usual core-to-surface temperature gradient. Specifically, an elevated gradient (core T minus cutaneous T) indicates the sympathetic vasoconstriction response to CHF, unless the air is cold or the vessels are constricted by mucosal sympathetic tone due, for example, to anxiety, or constricted by medication. A falling (normalizing) gradient is a sign of vasodilator therapy, a cornerstone of CHF therapy. A low gradient in CHF patient with a cool core T indicates high risk of death.

Whenever a change in temperature is detected that falls outside of a preselected criteria a signal is transmitted or an alarm triggered to notify the patient, the nurse, or the physician that a significant change in temperature has occurred. Examples of potential preselected criteria are when the patient's temperature decreases: a) more than 2° F. degrees from the admitting temperature, b) about 1° F. or more within 12 hours, c) about 2° F. or more over a 24 hour period, or d) about 1° F. or more over 24 hours if the baseline temperature of the patient is below 96.5° F. or falls two standard deviations below that patient's mean for the prior 24 hours.

Transmitted signals include text displays, noises, mild electric shocks, changes in color or shape, vibrations, warmth, or an electronic signal to a remote location such as a computer (including palm held device) or telephone system.

As shown in FIG. 4 an optional dual signaling system may be used. A first signal is sent when a first predetermined criteria is met or surpassed. This signal would most likely be sent to the nurses station to identify the patient as needing more intensive monitoring. This first signal may also initiate a change in the analysis program used to analyze the collected data. For example, the time criteria for taking measurements may be changed or the rate of temperature change allowed decreased to represent a stricter criteria. Whenever the patient's temperature falls beyond a second criteria, a second signal is transmitted or an alarm triggered indicating the patient may need left ventricular assistance or other more intensive therapy.

The ability to carefully monitor a CHF patient's body temperature may well help to save these patient's lives by providing notice of a change in prognosis in time to alter the therapy being administered. It may also provide a more accurate prognosis for the patients and their families.

E. Mortality Predictive Kit

Preferably a set of temperature monitoring devices are provided in an easy-to-use kit for identifying patients at imminent risk of dying from congestive heart failure. A suitable kit would include at least one device for monitoring the core body temperature of the patient, such as a Swan-Ganz catheter, IV needle, urinary catheter or the like, equipped with a temperature sensor such as a thermistor or thermocouple. A conventional tympanic ear temperature monitoring device or umbilicus temperature monitoring device could also be included for measuring the core body temperature. In addition, the kit would include at least one device for monitoring the temperature of cutaneous sites, such as the fingers, toes, upper arms, thighs, and optionally calves and forearms. The kit could also include electronic equipment for analyzing temperature signals and triggering an alarm if a dangerous decline in temperature is detected in the patient.

Alternatively, temperature sensors may be incorporated into other monitoring devices such that temperature and $O_2$ saturation and/or $pCO_2$ and/or blood pressure, change in width of the QRS or QT interval, or other parameters would be measured simultaneously and used to enhance the prediction of CHF mortality:

References

1. Myers J, Gullestad L, Vagelos R, et al. Clinical, hemodynamic, and cardiopulmonary exercise test determinants of survival in patients referred for evaluation of Heart failure. Ann Intern Med 1998; 129:286–93.
2. Ommen S R, Hodge D O, Rodeheffer R J, McGregor C G, Thomson S P, Gibbons R J. Predictive power of the relative lymphocyte concentration in patients with advanced heart failure [see comments]. Circulation 1998; 97:19–22.
3. Pierpont G L, Parenti C M. Physician risk assessment and APACHE scores in cardiac care units. Clin Cardiol 1999; 22:366–8.
4. Vranckx P, Van Cleemput J. Prognostic assessment of end-stage cardiac failure. Acta Cardiol 1998; 53:121–5.
5. Parameshwar J, Keegan J, Sparrow J, Sutton G C, Poole-Wilson P A. Predictors of prognosis in severe chronic heart failure. Am Heart J 1992; 123:421–6.
6. Bonaduce D, Petretta M, Marciano F, et al. Independent and incremental prognostic value of heart rate variability in patients with chronic heart failure. Am Heart J 1999; 138:273–84.
7. Teerlink J R, Jalaluddin M, Anderson S, et al. Ambulatory ventricular arrhythmias in patients with heart failure do not specifically predict an increased risk of sudden death. PROMISE (Prospective Randomized Milrinone Survival Evaluation) Investigators. Circulation 2000; 101:40–6.
8. Rouleau J, Shenasa M, de Champlain J, Nadeau R. Predictors of survival and sudden death in patients with stable severe congestive heart failure due to ischemic and nonischemic causes: a prospective long term study of 200 patients. Ccn J Cardiol 1990; 6:453–60.
9. Cohn J N, Rector T S. Prognosis of congestive heart failure and predictors of mortality. Am J Cardiol 1988; 62:25A-30A.
10. Adams K F, Jr., Sueta C A, Gheorghiade M, et al. Gender differences in survival in advanced heart failure. Insights from the FIRST study. Circulation 1999; 99:1816–21.
11. Hunt S A. Current status of cardiac transplantation. JAMA 1998; 280:1692–8.
12. Fox E, Landrum-McNiff K, Zhong Z, Dawson N V, Wu A W, Lynn J. Evaluation of prognostic criteria for determining hospice eligibility in patients with advanced lung, heart, or liver disease. SUPPORT Investigators. Study to Understand Prognoses and Preferences for Outcomes and Risks of Treatments [see comments]. Jama 1999; 282:1638–45.
13. Willenheimer R, Erhardt L R. Value of 6-min-walk test for assessment of severity and prognosis of heart failure. Lancet 2000; 355:515–6.
14. Robbins M, Francis G, Pashkow F J, et al. Ventilatory and heart rate responses to exercise. Better predictors of heart failure mortality than peak oxygen consumption. Circulation 1999; 100:2411–7.
15. Vasan R S, Larson M G, Benjamin E J, Evans J C, Reiss C K, Levy D. Congestive heart failure in subjects with normal versus reduced left ventricular ejection fraction: prevalence and mortality in a population-based cohort. J Am Coll Cardiol1999; 33:1948–55.
16. Senni M, Tribouilloy C M, Rodeheffer R J, et al. Congestive heart failure in the community: a study of all incident cases in Olmsted County, Minn., in 1991. Circulation 1998; 98:2282–9.
17. Ho K K, Moody G B, Peng C K, et al. Predicting survival in heart failure case and control subjects by use of fully automated methods for deriving nonlinear and conventional indices of heart rate dynamics. Circulation 1997; 96:842–8.
18. Anker S D, Ponikowski P, Varney S, et al. Wasting as independent risk factor for mortality in chronic heart failure [published erratum appears in Lancet 1997 Apr 26;349(9060):1258]. Lancet 1997; 349:1050–3.
19. Doval H C, Nul D R, Grancelli H O, et al. Nonsustained ventricular tachycardia in severe heart failure. Independent marker of increased mortality due to sudden death. Gesica-Gema Investigators [see comments]. Circulation 1996; 94:3198–203.
20. Shellock F G, Rubin S A. Mixed venous blood temperature response to exercise in heart failure patients treated with short-term vasodilators. Clin Physiol 1985; 5:503–14.
21. Shellock F G, Rubin S A, Ellrodt A G, Muchlinski A, Brown H, Swan H J. Unusual core temperature decrease in exercising heart-failure patients. J Appl Physiol 1983; 54:544–50.

Although the present invention and its advantages have been described in detail, it should be understood that various changes, substitutions, and alterations can be made to the described methods and apparatus without departing from the spirit and scope of the invention as defined by the appended claims.

What is claimed is:

1. A method of monitoring a patient with congestive heart failure for prognosis of survival, which comprises:
   (a) obtaining an initial body temperature which is not elevated above normal,
   (b) obtaining subsequent body temperatures of the patient and determining whether the subsequent temperatures fit any of predetermined criteria showing a condition of congestive heart failure hypothermia.

2. The method of claim 1 in which upon detection of a temperature less than normal temperature, core body temperature is monitored in step (b).

3. The method of claim 1 further characterized in that the initial body temperature is cutaneous and obtained as a pattern of base line temperatures from a plurality of surface sites on the patient, and step (b) includes analyzing the subsequent temperatures to determine variation of heat distribution over the body, and further including the step of (c) outputting an alarm if said heat distribution over the body exceeds a predetermined pattern indicative of congestive heart failure hypothermia.

4. The method of claim 1 in which said predetermined criteria showing a condition of congestive heart failure hypothermia include any one or more of:
   (i) a decrease in temperature of about 2° F. or more from said initial temperature,
   (ii) a decrease in temperature of 1° F. or more within a 12 hour period,
   (iii) a decrease in temperature of about 1° F. or more over 24 hours if the patient's mean temperature is at or below 96.5° F.,
   (iv) a decrease in mean temperature of two standard deviations below the patient's mean temperature over the prior 24 hours.

5. A method of predicting time remaining to death absent intervention for a patient with congestive heart failure, which comprises:
   (a) obtaining an initial body temperature which is not elevated above normal,
   (b) obtaining subsequent body temperatures of the patient and determining whether the subsequent temperatures fit any of predetermined criteria showing a condition of congestive heart failure hypothermia, and if so,
   (c) predicting time to death according to the formula:

Time to Death (hours)=12.5 (° F.−95.24)

where ° F. represents the current temperature of the patient.

6. A method of warning of imminent mortality in a patient suffering from congestive heart failure absent therapeutic intervention, comprising:
   (a) sensing internal and/or external temperatures of a patient
   (b) analyzing the temperatures to determine a data set conforming to a predefined condition signifying congestive heart failure hypothermia; and
   (c) issuing an alarm reporting said condition.

7. A method of predicting imminent mortality in a patient suffering from congestive heart failure, comprising:
   (a) determining an initial body temperature which is not in excess of 97° F.,
   (b) obtaining subsequent body temperatures of the patient and determining whether the subsequent temperatures fit any of a first set of predetermined criteria for a condition of developing congestive heart failure hypothermia, and if so,
   (c) monitoring the patient under a second set of predetermined criteria for a developed condition of congestive heart failure hypothermia and determining whether the subsequent temperatures fit any of said second set of predetermined criteria, and if so;
   (d) triggering an alarm for intensive therapy.

8. A method of predicting imminent mortality in a patient suffering from congestive heart failure, comprising:
   (a) determining an initial body temperature which is not in excess of 97° F.,
   (b) obtaining at least one temperature sensor for measuring a cutaneous body temperature and at least one sensor for measuring a core body temperature;
   (c) positioning said sensors to be in direct contact with a patient having said initial temperature;
   (d) transmitting said core body temperature and said cutaneous body temperature at predetermined timed intervals to a processor programmed to analyze said temperatures;
   (e) analyzing said core body temperature and said cutaneous body temperature to determine if said temperatures fall outside of a predetermined criteria for a decrease in the patient's temperature signifying a condition of congestive heart failure hypothermia; and
   (f) triggering an alarm if said temperatures fall outside of said predetermined criteria.

9. The method of claim 8 in which said predetermined criteria in step (e) comprise at least one of:
   (i) a decrease in temperature of about 2° F. or more from said initial temperature,
   (ii) a decrease in temperature of 1° F. or more within a 12 hour period,
   (iii) a decrease in temperature of about 1° F. or more over 24 hours if the patient's mean temperature is at or below 96.5° F.,
   (iv) a decrease in mean temperature of two standard deviations below the patient's mean temperature over the prior 24 hours.

10. Apparatus for monitoring a patient with congestive heart failure for prognosis of survival, comprising:
    (a) a temperature detector for sensing temperature of a patient and generating a signal representative of the sensed temperature
    (b) a mount of said temperature sensor for indwelling or external placement on the patient,
    (c) a data recorder for receiving said detector signals at timed intervals and using the signals to produce and store data representing temperatures of the patient sensed over time,
    (d) an analyzer for processing said stored data to determine a data set conforming to a predefined condition signifying congestive heart failure hypothermia and outputting a signal indicative of the condition, and
    (e) an alarm for receiving and reporting said output signal indicative of said condition.

11. The apparatus of claim 10 in which said predefined condition signifying congestive heart failure hypothermia is any one or more of:
    (i) a decrease in temperature of about 2° F. or more from said initial temperature,
    (ii) a decrease in temperature of 1° F. or more within a 12 hour period,
    (iii) a decrease in temperature of about 1° F. or more over 24 hours if the patient's mean temperature is at or below 96.5° F., (iv) a decrease in mean temperature of two standard deviations below the patient's mean temperature over the prior 24 hours.

12. The apparatus of claim 10 in which said mount is an indwelling medical device selected from the group consisting of a needle, tube, catheter, line, pacemaker, implanted pump and implanted defibrillator.

13. The apparatus of claim 12, wherein said tube is selected from the group consisting of a nasogastric tube, Dubbhoff tube, endotracheal tube, rectal tube, T-tubes, drain, and nasal probe.

14. The apparatus of claim 12, wherein said catheter is selected from the group consisting of a urinary catheter, pulmonary artery catheter, triple-lumen catheter, dialysis catheter, Hickman catheter, and infusion catheter.

15. The apparatus of claim 10, wherein said mount for external placement is selected from the group consisting of umbilical sensor, skin electrode, tempanic ear sensor, pulse oximeter, and casts.

16. The apparatus of claim 10 in which said temperature detector is selected from the group consisting of a thermocouple, thermistor, thermosensitive chromophore, thermosensitive liquid crystal, infrared detector and ultrasound detector.

17. The apparatus of claim 10 further including means providing one or more additional predictors including one or more of $O_2$ saturation, $P_ACO_2$, pH, respiratory rate, QRS width, R—R variability and T wave alternans, heart rate, blood pressure, pulse pressure and dP/dt, as a composite index to maximize sensitivity and specificity.

18. Apparatus comprising:
(1) means for monitoring a patient with congestive heart failure for prognosis of survival, including:
   (a) a temperature detector for sensing temperature of a patient and generating a signal representative of the sensed temperature
   (b) a mount of said temperature sensor for indwelling or external placement on the patient,
   (c) a data recorder for receiving said detector signals at timed intervals and using the signals to produce and store data representing temperatures of the patient sensed over time,
   (d) an analyzer for processing said stored data to determine a data set conforming to a predefined condition signifying congestive heart failure hypothermia and outputting a signal indicative of the condition, and
   (e) an alarm for receiving and reporting said output signal indicative of said condition; and
(2) means of furnishing therapeutic warming to the patient.

19. A temperature monitoring kit for identifying a patient at risk of imminent death due to congestive heart failure, the kit comprising:
(a) at least one device for measuring a core temperature of a patient;
(b) at least one device for measuring a cutaneous temperature of the patient;
(c) means for transmitting the temperature measurements taken by said core temperature measuring device and said cutaneous temperature measuring device;
(d) means for analyzing the transmitted temperature measurements; and
(e) an alarm for reporting a dangerous decline in temperature in said patient.

20. The temperature monitoring kit of claim 19, wherein said core temperature measuring device includes a temperature detecting means attached to an indwelling or attached medical device.

21. The temperature monitoring kit of claim 19, wherein said cutaneous measuring device is selected from the group of umbilical sensor, skin electrode, and tympanic ear sensor.

22. The temperature monitoring kit of claim 19, wherein said analyzing means includes a processor programmed to identify when the temperature measurement transmitted to the analyzing means fall outside of a predetermined criteria.

23. The temperature monitoring kit of claim 22, wherein said predetermined criteria include any one of:
(i) a decrease in temperature of about 2° F. or more from said initial temperature,
(ii) a decrease in temperature of 1° F. or more within a 12 hour period,
(iii) a decrease in temperature of about 1° F. or more over 24 hours if the patient's mean temperature is at or below 96.5° F.,
(iv) a decrease in mean temperature of two standard deviations below the patient's mean temperature over the prior 24 hours.

24. The temperature monitoring kit of claim 19 wherein the alarm notifies a person of a change in the patient's temperature, said notification including a text display, noise, shock, change in color or shape, warmth, or vibration.

25. The temperature monitoring kit of claim 19 further including means providing one or more additional predictors including one or more of $O_2$ saturation, $P_ACO_2$, pH, respiratory rate, QRS width, R—R variability and T wave alternans, heart rate, blood pressure, pulse pressure and dP/dt, as a composite index to maximize sensitivity and specificity.

26. A temperature monitoring kit for identifying a patient at risk of imminent death due to congestive heart failure, the kit comprising:
(a) at least one device for measuring a core temperature of a patient, wherein said core temperature measuring device includes a temperature detecting means attached to an indwelling or attached medical device;
(b) at least one device for measuring a cutaneous temperature of the patient, wherein said cutaneous measuring device is selected from the group of an umbilical sensor, skin electrode, and tympanic ear sensor;
(c) means for transmitting the temperature measurements taken by said core temperature measuring device and said cutaneous temperature measuring device;
(d) means for analyzing the transmitted temperature measurements, wherein said analyzing means includes a processor programmed to identify when the temperature measurement transmitted to the analyzing means has decreased about 1° F. or greater within a 12 hour period, about 2° F. or greater over a 24 hour period, or about 1° F. or greater if the patient's baseline temperature is at or below 96.5° F. or two standard deviations below the patient's mean temperature for the prior 24 hours; and
(e) an alarm for reporting a dangerous decline in temperature in said patient, wherein the alarm notifies a person of a change in the patient's temperature, said notification including a text display, noise, shock, change in color or shape, warmth, or vibration.

27. A device for analyzing temperature measurements comprising a processor programmed to activate an alarm if a core body temperature of a patient suffering from congestive heart failure and exhibiting a hypothermic baseline temperature of 97° F. or less has (i) a decrease in temperature of about 2° F. or more from said initial temperature, (ii) a decrease in temperature of 1° F. or more within a 12 hour period, (iii) a decrease in temperature of about 1° F. or more over 24 hours if the patient's mean temperature is at or below 96.5° F., (iv) a decrease in mean temperature of two standard deviations below the patient's mean temperature over the prior 24 hours.

28. A device for analyzing temperature measurements comprising a processor programmed to activate an alarm if a temperature gradient between a core body temperature and a surface body temperature exceeds a predetermined criteria determined to signify congestive heart failure hypothermia.

29. Apparatus for providing alarm of imminent mortality in a patient suffering from congestive heart failure, comprising means for initially and subsequently obtaining body temperatures of a patient of 97° F. and lower and determining whether the subsequent temperatures lower than 97° F. fit any of a first set of predetermined criteria for a condition of developing congestive heart failure hypothermia, and if so, monitoring the patient under a second set of predetermined criteria for a developed condition of congestive heart failure hypothermia and determining whether the subsequent temperatures fit any of said second set of predetermined criteria, and if so, triggering an alarm for intensive therapy.

30. A temperature sensor comprising a temperature measuring device, said measuring device having means for notifying a patient diagnosed with congestive heart failure when the patient's temperature decreases below any one or more of predetermined criteria evidencing a condition of congestive heart failure hypothermia.

31. The temperature sensor of claim 30, wherein said sensor is attached to the patient's wristwatch, clothing, or clothing accessories.

* * * * *

UNITED STATES PATENT AND TRADEMARK OFFICE
CERTIFICATE OF CORRECTION

PATENT NO.         : 6,454,707 B1
APPLICATION NO.    : 09/519122
DATED              : September 24, 2002
INVENTOR(S)        : Samuel W. Casscells, III et al.

It is certified that error appears in the above-identified patent and that said Letters Patent is hereby corrected as shown below:

Please insert the following paragraph on Col. 1, of U.S. Patent No. 6,454,707 at line 10:

--STATEMENT REGARDING FEDERALLY SPONSORED RESEARCH OR DEVELOPMENT
      The U.S. Government has a paid-up license in this invention and the rights in limited circumstances to require the patent owner to license others on reasonable terms as provided for by the terms of Grant No. DAMD17-98-1-8002 awarded by U.S. Army Medical Research and Materiel Command.--

Signed and Sealed this

Fourteenth Day of April, 2009

JOHN DOLL
*Acting Director of the United States Patent and Trademark Office*